United States Patent [19]

Campbell et al.

[11] Patent Number: 4,626,241
[45] Date of Patent: Dec. 2, 1986

[54] APPARATUS AND METHOD FOR CONTROLLING THE PARENTERAL ADMINISTRATION OF FLUIDS

[75] Inventors: Peter Campbell, Lawrenceville; Izrail Tsals, Princeton Junction, both of N.J.; David Matsuura, La Jolla, Calif.

[73] Assignee: Ivac Corporation, San Diego, Calif.

[21] Appl. No.: 708,829

[22] Filed: Mar. 6, 1985

[51] Int. Cl.⁴ ..................... A61M 31/00; A61M 5/005
[52] U.S. Cl. ..................................... 604/49; 604/250; 251/7; 251/65
[58] Field of Search ..................................... 604/65–67, 604/152, 246, 249–250; 128/1 R, 346, DIG. 12, DIG. 13; 251/7, 65

[56] References Cited

U.S. PATENT DOCUMENTS

| | | |
|---|---|---|
| 3,756,556 | 9/1973 | Georgi . |
| 3,800,794 | 4/1974 | Georgi . |
| 3,817,237 | 6/1974 | Bolduc ................................. 604/250 |
| 3,890,968 | 6/1975 | Pierce et al. .......................... 604/65 |
| 4,038,981 | 8/1977 | LeFevre et al. ............. 128/DIG. 13 |
| 4,261,356 | 4/1981 | Turner et al. ........................ 604/250 |
| 4,262,824 | 4/1981 | Hrynewycz .......................... 604/250 |
| 4,266,697 | 5/1981 | Zissimopoulos ........................ 251/7 |
| 4,519,792 | 5/1985 | Dawe .................................... 604/152 |
| 4,541,429 | 9/1985 | Prosl et al. ........................... 604/249 |

Primary Examiner—John D. Yasko
Assistant Examiner—Michelle N. Lester
Attorney, Agent, or Firm—Fulwider, Patton, Rieber, Lee & Utecht

[57] ABSTRACT

An improved method and apparatus for controlling the flow rate in the parenteral administration of medical fluids, wherein a stored energy solenoid is utilized to move a pincher element against and away from a flexible IV tube in a repetitive manner to thereby control the flow of fluids through the tube.

19 Claims, 10 Drawing Figures

APPARATUS AND METHOD FOR CONTROLLING THE PARENTERAL ADMINISTRATION OF FLUIDS

BACKGROUND OF THE INVENTION

This invention relates generally to the field of fluid flow control devices and particularly to an energy efficient flow control device for the parenteral administration of medical fluid through an intravenous tube.

The usual procedure for the parenteral administration of fluids into the human body utilizes an intravenous set comprising a bottle of liquid supported in an inverted position, a flexible, clear plastic intravenous tube for delivery of fluid to the patient, a drip chamber and a suitable valve mechanism, such as a roller clamp attached to the tube to control the flow of fluid out of the bottle into a drip chamber below the bottle. The most simple way of controlling the fluid fed to a patient is to count the drops dripping into the drip chamber over a period of time, and to adjust roller clamp to provide the flow rate as needed.

Administration of the medical liquids by gravity in the aforesaid manner is subject to large flow rate variations due to a variety of well known causes and in recent years, sophisticated electronic monitoring systems and drop controllers have been developed to minimize such flow variations.

One very successful improvement in drop rate controllers is disclosed in U.S. Pat. No. 3,800,794 to H. W. Georgi (assigned to the present assignee) entitled METHOD AND APPARATUS FOR FLUID FLOW CONTROL. In this patent, an electronic system is described which controls the frequency at which a pincher opens and closes an IV tube to a relatively high multiple of the drop rate.

Another advance in the art is disclosed in U.S. Pat. No. 3,756,556 to H. W. Georgi (assigned to the present assignee) entitled FLUID FLOW CONTROL APPARATUS which describes an improved electromechanical device for controlling fluid flow.

The above inventions are embodied in infusion controllers (Models 230 and 260) manufactured by IVAC Corporation. While IVAC controllers embodying the Georgi inventions have been commercially successful, the need for even further improvement has remained. The present invention satisfies that need and provides a compact, quiet energy efficient flow controller having durability and long term accuracy.

BRIEF DESCRIPTION OF THE INVENTION

The present invention relates to an improved method and apparatus for controlling the drop flow rate in the parenteral administration of medical liquids wherein a stored energy solenoid is utilized to move a pincher element so that an IV tube is rapidly and repetitively opened and closed to thereby control the medical liquids passing through the tube to a patient.

In accordance with the invention, a high energy permanent magnet, such as the samarium-cobalt and neodymium-iron type magnet, urges the pincher element against an IV tube to constrict the tube and thereby essentially stop fluid flow through the flexible tube. The pincher element is attached to a spring or other means so that, when the first force produced or developed by the permanent magnet urges the pincher against the IV tube, a second force, opposite in direction to that developed by the permanent magnet, is applied to the pincher by the spring or other means. However, the magnitude of the second force applied by the spring or other means is not sufficient to completely counteract the first force applied by the permanent magnet and to move the pincher away from the IV tube so as to affect fluid flow through the tube. Means are provided to periodically reduce the force applied by the permanent magnet so that the pincher will move away from the tube to open up the tube and thereby start or increase fluid flow through the tube.

In a preferred embodiment an electromagnetic coil is provided to generate a magnetic flux in the core of the coil, air gap and armature that is opposite in direction to the flux generated in the core and air gap by the permanent magnet and this reduces the first force applied to the pincher by the permanent magnet. When the electrical current flowing through the coil is sufficiently high, the first force applied to the pincher by the permanent magnet can be reduced to a level less than the sum of the force applied by the spring and the small amount of force applied to the pincher bar by the tube. When this occurs, the pincher moves away from the IV tube and thereby allows fluid to flow through the tube. When the electical current flow through the coil is terminated, the first force from the permanent magnet again urges the pincher against the IV tube to essentially stop liquid flow. By passing electrical current through the coil in a periodic or repetitive manner the pincher element can open and close the IV tube in a periodic or repetitive manner, and preferably at a frequency which is a relatively high multiple of the drop rate. A frequency of about 1 to 20 Hz is preferred.

It has been determined empirically that a force of about one to two pounds is required to close off completely commercially available plastic IV tubing. Thus, when the pincher closes the IV tube and the spring is elastically bent, the additional differential force on the pincher element must be at least the two pounds in order to keep the tube closed. The magnitude of the force applied by the permanent magnet is preferably kept as small as possible to minimize the size of the actuator assembly. A force of about 3-6 pounds has been found suitable. The differential force between the spring and the magnet is preferably about 2 to 10 pounds.

By utilizing the permanent magnet to provide the force on the pincher to close the IV tube and by energizing the coil only to release the pincher, the entire unit can be consolidated into a very small package, much smaller than that previously employed. Moreover, due to the small amount of energy required to operate the unit, it is quiet, durable and very reliable in performing the desired function. Additionally, due to the low energy requirements, battery operated devices can remain operational over much longer periods of time.

These and other advantages of the invention will become more apparent from the following detailed description of a preferred embodiment when taken in conjunction with the attached drawings.

DESCRIPTION OF THE DRAWINGS

In the drawings all corresponding parts are numbered the same. The drawings have been greatly simplified for purposes of illustration.

DETAILED DESCRIPTION OF A PREFERRED EMBODIMENT

Reference is made to the above drawings which illustrate a controller embodying features of the invention and the basic principles thereof.

Figure 1:
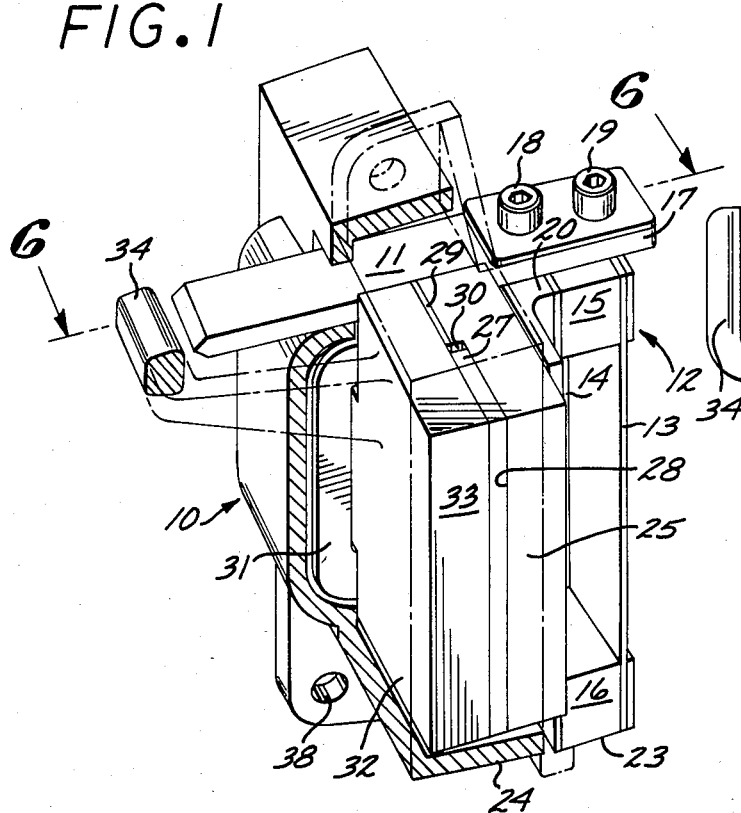
FIG. 1 is a perspective cut away view of the operating elements of a controller or actuator assembly embodying features of the invention.
Figure 2:
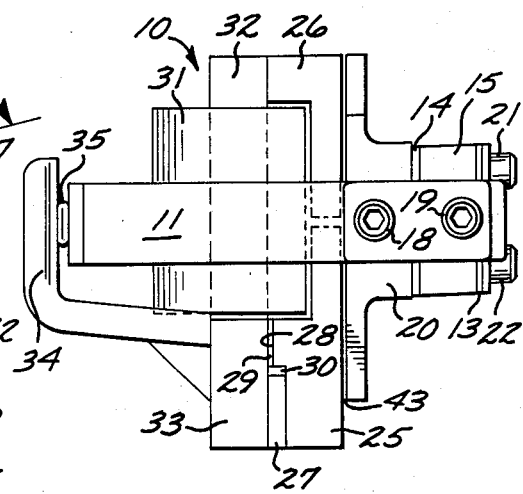
FIG. 2 is a top view showing the pincher pressed against and closing an IV tube.
Figure 3:
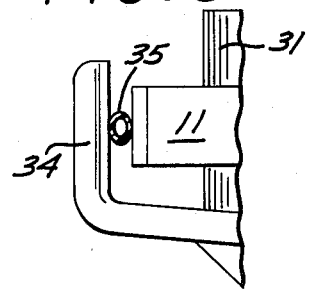
FIG. 3 is a partial top view equivalent to FIG. 2 but showing the position of the pincher with an opened tube.

With particular reference to FIGS. 1-3, the controller or actuator assembly 10 comprises a pincher 11 fixed to a spring assembly 12 comprising two parallel ribbon or leaf springs 13 and 14 separated and supported at both ends by spacer blocks 15 and 16. The non-operative end 17 of pincher 11 is fixed to the spacer block 15 by suitable bolts 18 and 19. A moving armature 20 is also fixed to the non-operating end 17 of the pincher 11 by bolt 18 and to spacer block 15 by bolts 21 and 22. The spring assembly 12 is cantilevered from end 23 thereof to allow the movement of the pincher 11 and armature 20. Adjacent to the moving armature 20 are two separate pole pieces 24 and 25 which are fixed to the support frame 26 by means not shown. A permanent magnet 27 is attached to side 28 of pole piece 24 and a magnetic shunt 29, preferably a brass shim or other non-magnetic material, is also attached to side 28 adjacent to the permanent magnet 27, with an air gap 30 therebetween. An electromagnetic coil 31 is positioned between the pole pieces 24 and 25 and is provided with a key-shaped iron core 32 disposed, at least in part, within the center of coil 31. As shown best in FIG. 1, the larger section 33 of core 32 is more or less co-extensive with the pole piece 24 adjacent thereto which contains the brass shim 29 and the permanent magnet 27. The magnetic shunt 29 maintains an appropriate spacing between the pole piece 24 and larger section 33 of core 32 to maintain a desired level of magnetic flux passing therethrough. Preferably, at least 40% of the flux passes through the shunt.

A finger element 34 is provided to support a flexible plastic tube 35, and it is suitably fixed to the support frame 26 as shown in phantom in FIG. 1.

FIGS. 2 and 3, which are top views of the controller unit, illustrate the closing and opening of the plastic tube 35 by the pincher 11. When the tube 35 is opened, it is usually only partially open, as shown in FIG. 3.

Figure 4:
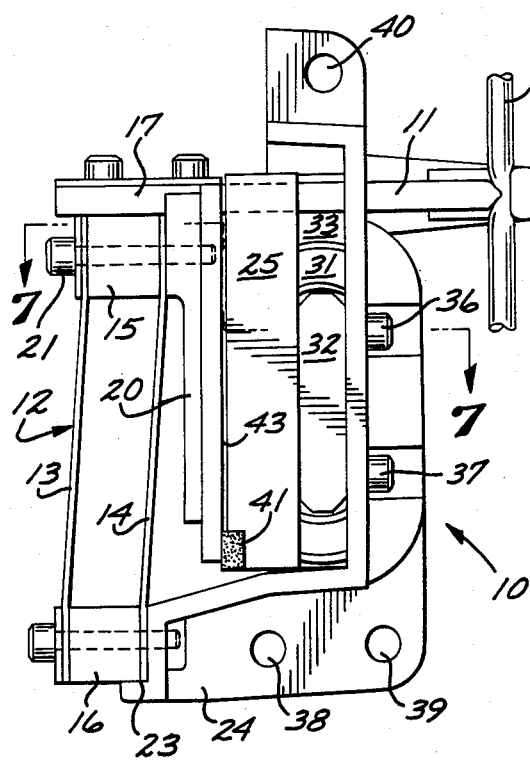
FIGS. 4 and 5 are left side views showing the relative position of the members when the pincher has closed the tube and when the pincher has moved away from the tube to allow the opening thereof.
Figure 5:
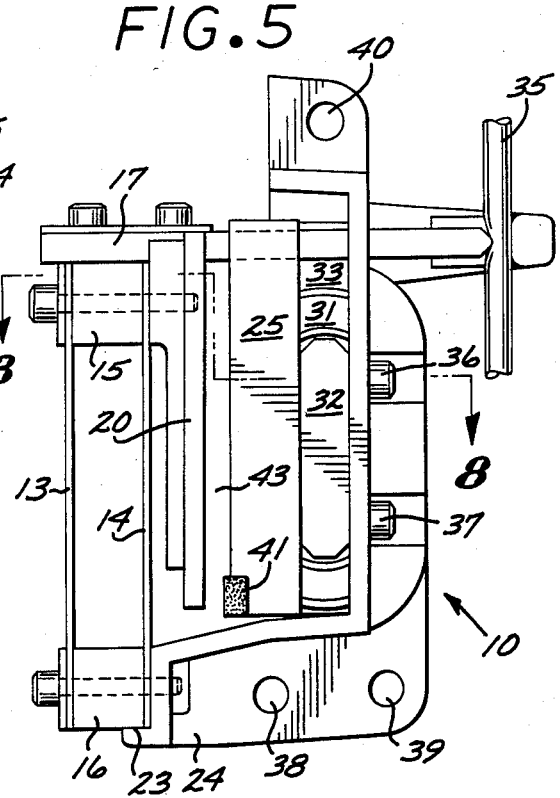
Figure 6:
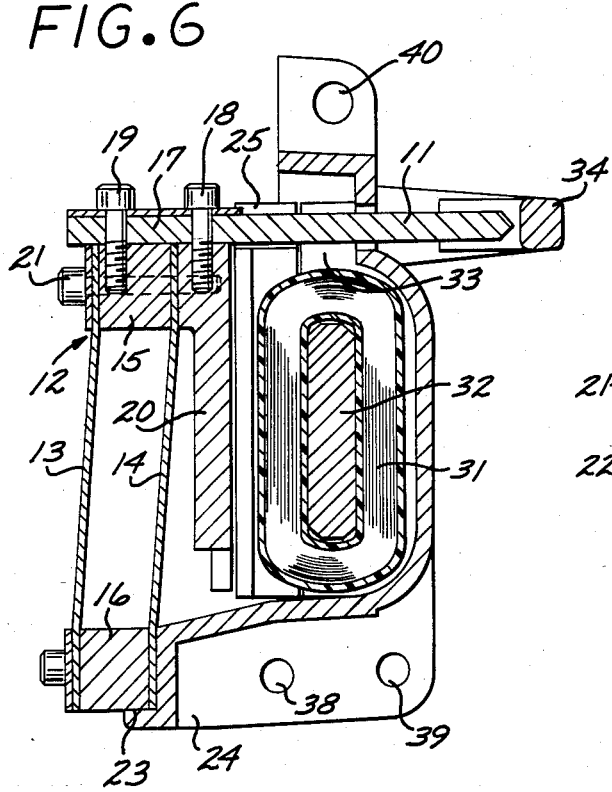
FIG. 6 is a cross-sectional view taken along the lines 6—6 shown in FIG. 1.

The side views of the assembly 10 in FIGS. 4 and 5 illustrate the relative positions of the assembly members when the IV tube is closed and opened. In the closed position, the armature 20 is closely positioned to the pole pieces 24 and 25 with the non-magnetic spacer pads 41 and 42 maintaining the minimum air gaps 43 and 44.

Figure 7:
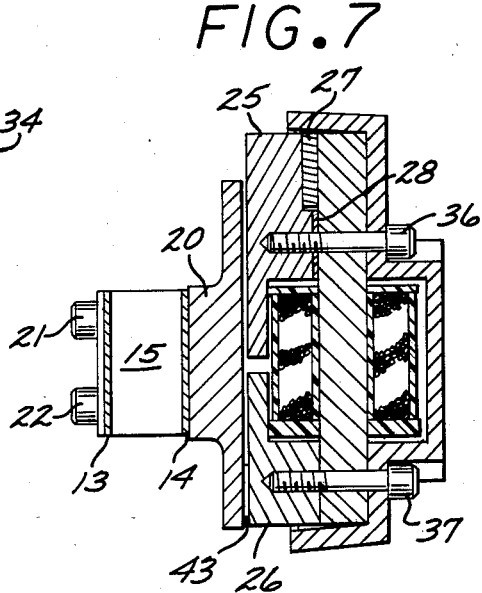
FIGS. 7 and 8 are respectively, cross-sectional views of FIGS. 4 and 5 taken along the lines of 7—7 and 8—8 respectively.
Figure 8:
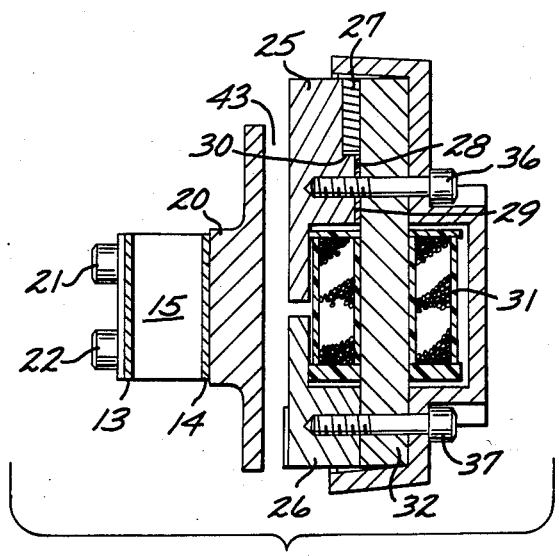

As best shown in FIGS. 7 and 8, the core 32 and the pole pieces 24 and 25 are supported by bolts 36 and 37 to support frame 26. The support frame 26 in turn is fixed to a housing (not shown) by means of bolts which pass through apertures 38, 39 and 40.

Figure 9:
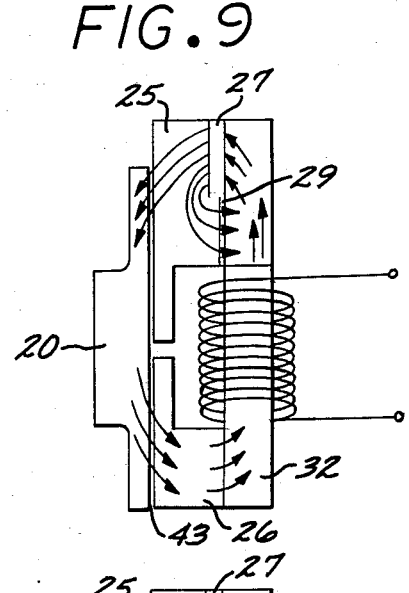
FIGS. 9 and 10 are schematic views showing the relative positions of the operative members of the assembly and illustrating the flow of magnetic flux during the operation of the assembly.
Figure 10:
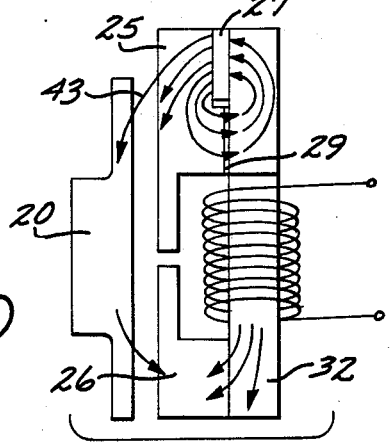

The operation of the controller assembly 10 is further illustrated in FIGS. 9 and 10 which schematically illustrate the dual path of magnetic flux during the operation thereof. As shown in FIG. 9, the magnetic flux from the permanent magnet 27 passes through pole piece 24 across the gap 43 through armature 20, across the gap 44 into pole piece 25 and then into core 32. The flux passes through the core 32 within the coil 31 and then back to the other pole or face of the permanent magnet 27. Part of the flux from the permanent magnet 27 passes from the pole piece 24 across the shunt 29 into the core 32 where it returns to the opposite pole or face of the permanent magnet 27. As shown in FIG. 10, when electric current passes through the coil 31 a magnetomotive force is generated which counters the magnetic flux passing through the core 32 from the permanent magnet 27. This causes a substantial reduction in the flux passing through moving armature 20, thus reducing significantly the force on the armature 20 which urges the pincher 11 against the IV tube 35. When the attractive force on the armature is reduced, the gaps 43 and 44 between armature 20 and the pole pieces 24 and 25, respectively, increase due to the force of the spring assembly 12 on the armature 20 opposite in direction. As a result the pincher 11 moves away from the IV tube 35 thereby opening up the tube. When the electrical current flowing through the coil 31 is terminated, the armature 20, attached to the ribbon spring assembly 12, is again attracted by the permanent magnet 27 so that the gaps 43 and 44 are narrowed and the magnetic flux again passes through the armature. By initiating and terminating electrical current flow through the coil 31 in a repetitive manner the pincher 11 can be reciprocated toward and away from the flexible tube 35, and as a result thereof, cause fluid to flow therein in a pulsating or peristaltic manner. The actuator assembly is designed to operate at a frequency of about 1 to about 20 Hz, although with modifications, well known to those skilled in the art, the frequencies can be increased up to about 40 Hz.

The size of the electrical coil 31 necessary to reduce the magnetic force on the armature 20 and thus the pincher 11 need not be very large or powerful because the force required to move the pincher 11 away from the plastic tube 35 is relatively small, i.e., on the order of about 1 to 2 pounds. Because of the low power requirements, the controller assembly 10 can be operated at a much lower sound level than prior art devices and the entire assembly 10 can be made much smaller than the prior art devices without detrimentally affecting the reliability and durability of the controller assembly.

Various modifications and improvements can be made to the present invention without departing from the inventive concepts thereof.

We claim:

1. A method of controlling the flow of fluid through a flexible tube comprising:
   a. applying a first force to a pincher element by means of a permanent magnet to urge the pincher element against the tube;

b. applying a second force to the pincher element which is essentially opposite in direction and which is smaller in magnitude than the first force so that the resultant force urging the pincher element against the tube is sufficient to constrict the tube and to thereby essentially stop fluid flow through the tube; and c. reducing the first force to a magnitude less than the sum of the magnitude of the second force and any force applied to the pincher element by the tube so that the resultant force on the pincher element will cause the pincher element to move away from its position constricting the tube, thereby opening up the tube and allowing fluid flow through the tube.

2. The method of claim 1 wherein the reduction in the force applied to the pincher element by the magnetic means is effected by the operation of an electromagnetic coil which develops a magnetic flux opposite in direction to the flux from the permanent magnet.

3. The method of claim 2 wherein the electromagnetic coil is operated repetitively so that the pincher element is moved against and away from the tube repetitively.

4. The method of claim 3 wherein the electromagnetic coil is operated at a frequency of about 1 to about 20 Hz.

5. In an apparatus to control the flow of fluid through a flexible tube wherein a pincher element is urged against the tube to constrict the tube and thereby essentially stop fluid flow therethrough and wherein the pincher element is moved away from its position against the tube to allow fluid flow therethrough, the improvement comprising:

a. a permanent magnet means to apply a first force to the pincher element to thereby urge the pincher element against the tube, b. a second means to apply a second force to the pincher element which is opposite in direction but smaller in magnitude than the first force applied thereto; and c. means to reduce the first force applied to the pincher element to a magnitude less than the sum of the force applied to the pincher element by the second means and any force applied to the pincher element by the tube to thereby move the pincher element away from its position constricting the tube.

6. The apparatus of claim 5 wherein the second force applying means is spring actuated.

7. The apparatus of claim 5 wherein the means to reduce the first force applied by the permanent magnet to the pincher element is an electromagnetic means.

8. The apparatus of claim 7 wherein the electromagnetic means operates repetitively at a frequency of about 1 to about 20 Hz.

9. The apparatus of claim 5 wherein the permanent magnetic means is selected from the group consisting of samarium-cobalt and neodymium type magnets.

10. The apparatus of claim 9 wherein an armature is attached to the pincher element and is attracted by the permanent magnet to thereby force the pincher element against the tube to constrict the tube.

11. The apparatus of claim 7 wherein the electromagnetic means is a coil with a core which generates a magnetic flux when actuated that reduces the magnetic flux in the core generated by the permanent magnetic means and thereby reduces the first force applied to the pincher element by the magnetic means.

12. The apparatus of claim 11 wherein two independent pole pieces are provided between the armature and the core to thereby complete the electromagnetic circuit between the permanent magnetic means, the core and armature.

13. The apparatus of claim 12 wherein the permanent magnetic means is fixed to one of the pole pieces on the side thereof adjacent to the core.

14. The apparatus of claim 13 wherein an magnetic shunt is provided between the core and the pole piece to which the permanent magnet is fixed.

15. The apparatus of claim 14 wherein the shunt is a brass shim.

16. The apparatus of claim 15 wherein at least 40% of the magnetic flux passes through the shunt.

17. The apparatus of claim 6 wherein the spring actuated means has at least one flat elongated ribbon or leaf spring which is secured at one end thereof to a support frame and secured at the other end thereof to the pincher element.

18. In a system for the administration of parenteral fluids to a patient wherein parenteral fluid is withdrawn or drained from a container and passed through a flexible tube to the patient, and wherein a pincher element is forced against the tube to construct the tube and thereby essentially stop fluid flow therethrough and wherein the pincher element is withdrawn from its position against the tube to allow fluid flow therethrough, the improvement comprising:

a. a permanent magnet means to apply a first force against the pincher element to urge the pincher element against the tube, b. a means to apply a second force to the pincher element which is opposite in direction but smaller in magnitude than the first force; and c. means to reduce the first force applied to the pincher element to a magnitude less than the sum of the second force applied to the pincher element and any force applied to the pincher element by the tube.

19. In a method of administering parenteral fluids to a patient wherein parenteral fluid is withdrawn or drained from a container and passed through a flexible tube to the patient, the improvement in controlling the flow of fluids through the flexible tube to the patient comprising:

a. applying a first force to a pincher element by means of a permanent magnet to urge the pincher element against the tube to constrict the tube and thereby essentially stop fluid flow through the tube;

b. applying a second force to the pincher element which is essentially opposite in direction and which is smaller in magnitude that the first force applied to the pincher element; and c. reducing the first force applied to the pincher element to a magnitude less than the sum of the magnitude of the second force and any force applied to the pincher bar by the tube to cause the pincher element to move away from its position constricting the tube and thereby allow fluid flow through the tube.

* * * * *